United States Patent [19]

Schmerling

[11] 4,088,820
[45] May 9, 1978

[54] TRANSESTERIFICATION OF OLEFINS

[75] Inventor: Louis Schmerling, Riverside, Ill.

[73] Assignee: UOP Inc., Des Plaines, Ill.

[21] Appl. No.: 736,649

[22] Filed: Oct. 28, 1976

[51] Int. Cl.$^2$ .................... C07C 67/00; C07C 69/14; C07C 69/78
[52] U.S. Cl. ........................................ 560/103; 560/1; 560/106; 560/247
[58] Field of Search .................. 260/476 R, 469, 491, 260/468 R; 560/1, 103, 106, 247

[56] References Cited
U.S. PATENT DOCUMENTS 4,009,203 2/1977 Schmerling ..................... 260/476 R Primary Examiner—Jane S. Myers
Attorney, Agent, or Firm—James R. Hoatson, Jr.; Raymond H. Nelson; William H. Page, II

[57] ABSTRACT

Olefins may be esterified by reaction with esters of saturated alcohols containing at least two carbon atoms in the presence of a catalytic amount of a tin halide catalyst, the reaction being effected at temperatures ranging from about 0° to about 150° C.

9 Claims, No Drawings

TRANSESTERIFICATION OF OLEFINS

BACKGROUND OF THE INVENTION

Heretofore, it has been believed that when effecting a reaction with compounds containing oxygen such s first stage oxygenated compounds including alochols, second stage oxygenated roducts such as aldehydes or ketones, or third stage oxygenated compounds such as acids, the reaction would require the presence of stoichiometric amounts of metal halides such as aluminum chloride. However, as will hereinafter be shown in greater detail, it has now been discovered that esters of the specified structure may be reacted with olefins in the presence of a catalytic amount, that is, less than a stoichiometric quantity as compared to the olefin, of a tin halide whereby the olefin may be esterified. By being able to utilize only catalytic amounts of the tin halide, it is possible to prepare the desired compounds at a relatively low cost, and thus render the process more attractive from an economic standpoint.

This invention relates to a process for the esterification of an olefin. More specifically the invention is concerned with a process for the transesterification of an ester with an olefin, said reaction being effected in the presence of a tin halide.

As hereinbefore set forth, it has now been discovered that certain types of esters may be reacted with an olefin to effect a transesterification reaction which results in the formation of an ester of the olefin. This transesterification reaction is of relative importance in the chemical industry inasmuch as the reaction offers a means of obtaining esters which otherwise would have to be prepared in a more difficult manner. Esters will find a wide variety of uses in the chemical field. For example, secbutyl acetate is used as a solvent for nitrocellulose, lacquers, thinners, nail enamels, celluloid products, etc.; sec-heptyl formate is used in artificial fruit essances; sec-octyl acetate is used in perfumery and flavors; ect.

It is therefore an object of this invention to provide a transesterification process.

A further object of this invention is to provide a process for the transesterification of an ester with an olefin which comprises reacting the compounds in the presence of a tin halide.

In one aspect an embodiment of this invention resides in a process for the transesterification of an ester of a saturated alcohol containing at least two carbon atoms with an olefin which comprises reacting said olefin with an ester in the presence of a tin halide catalyst at reaction conditions, and recovering the resultant esterified olefin.

A specific embodiment of this invention is found in a process for the transesterification of an ester of an alcohol containing at least two carbon atoms with an olefin which comprises reacting 7-tetradecene with cyclohexyl acetate in the presence of anhydrous stannic chloride at a temperature in the range of from about 0° to about 150° C. and a pressure in the range of from about atmospheric to about 100 atmospheres, and recovering the resultant tetradecyl acetate.

Other objects and embodiments will be found in the following further detailed description of the present invention.

As hereinbefore set forth the present invention is concerned with a process for the transesterification of an ester wherein an olefin is reacted with an ester in the presence of a tin halide catalyst. The reaction is effected under operating conditions which will include a temperature in the range of from about 0° to about 150° C., and preferably in a range of from about 40° to about 100° C. In addition to operating within the aforementioned temperatures, the reaction is also effected at pressures which may range from about atmospheric to about 100 atmospheres, said superatmospheric pressures being effected by employing a substantially inert gas such as nitrogen, argon, helium, the amount of pressure which is employed being that which is sufficient to maintain a major portion of the reactants in the liquid phase.

Suitable esters which may be employed in the transesterification reaction of the present invention will include alkyl, cycloalkyl, and aralkyl esters in which the alkyl moiety contains at least two carbon atoms. Examples of the alkyl esters include ethyl formate, propyl formate, butyl formate, amyl formate, hexyl formate, heptyl formate, octyl formate, nonyl formate, decyl formate and formates of higher molecular weight alkyl groups containing up to about 20 carbon atoms; ethyl acetate, propyl acetate, butyl acetate, amyl acetate, hexyl acetate, heptyl acetate, octyl acetate, nonyl acetate, decyl acetate and acetates of higher molecular weight alkyl groups containing up to about 20 carbon atoms; ethyl propionate, propyl propionate, butyl propionate, amyl propionate, hexyl propionate, heptyl propionate, octyl propionate, nonyl propionate, decyl propionate, and propionates of higher molecular weight alkyl groups containing up to about 20 carbon atoms; ethyl butyrate, propyl butyrate, butyl butyrate, amyl butyrate, hexyl butyrate, heptyl butyrate, octyl butyrate, nonyl butyrate, decyl butyrate, etc.; cycloalkyl esters such as cyclopentyl formate, cyclohexyl formate, cycloheptyl formate, cyclooctyl formate, cyclopentyl acetate, cyclohexyl acetate, cycloheptyl acetate, cyclooctyl acetate, cyclopentyl propionate, cyclohexyl propionate, cycloheptyl propionate, cyclooctyl propionate, cyclopentyl butyrate, cyclohexyl butyrate, cycloheptyl butyrate, cyclooctyl butyrate, etc., including alkylcycloalkyl esters such as ethyl cyclohexylate, propyl cyclohexylate, butyl cyclohexylate, etc., aryl esters such as betaphenylethyl acetate, 3-p-tolylpropyl butyrate, etc. Esters formed from saturated alcohols containing at least two carbon atoms and aromatic acids such as benzoic acid, toluic acids, etc., are also considered within the scope of this invention. It is to be understood that the esters herein listed are only representative of the class of esters which may be employed, and that the present invention is not necessarily limited thereto.

Examples of olefins which are reacted with the ester will include alkenes, either straight or branched chained in configuration containing from 2 to about 20 carbon atoms per molecule and cycloalkenes which contain from 4 to about 8 carbon atoms in the ring. Specific examples of these olefins will include ethylene, propylene, 1-butene, 2-butene, isobutene, 1-pentene, 2-pentene, 1-hexene, 2-hexene, 3-hexene, 1-heptene, 2-heptene, 3-heptene, the isomeric straight chained octenes, nonenes, decenes, undecenes, dodecenes, tridecenes, tetradecenes, pentadecenes, hexadecenes, heptadecenes, octadecenes, nonadecenes, eicosenes; branched chained isomers of these compounds such as 2-methyl-1-pentene, 2-methyl-2-pentene, 3-methyl-1-pentene, 3-methyl-2-pentene, 2-methyl-1-hexene, 2-methyl-2-hexene, 2-methyl-3-hexene, 3-methyl-1-hexene, 1,2-dimethyl-3-hexene, 1-methyl-1-heptene, 1-methyl-2-heptene, ect.;

cyclobutene, cyclopentene, cyclohexene, cycloheptene, cyclooctene, 1-methyl-1-cyclopentene, 1-methyl-1-cyclohexene, 1-methyl-1-cycloheptene, 1-methyl-1-cyclooctene, etc. It is to be understood that the aforementioned olefins are only representative of the class of compounds which may be employed and that the present invention is not necessarily limited thereto.

The transesterification of the ester is accomplished by reacting said ester with the olefin in the presence of a catalytic amount, based on the olefin, of a tin halide. In the preferred embodiment the tin halide compound will comprise a halide of tin in its highest valence state, that is, stannic chloride, stannic bromide, stannic iodide, etc., the preferred catalyst due to its greater availability and greater activity comprising stannic chloride and preferably in an anhydrous form. It is also contemplated within the scope of this invention that hydrated forms of the stannic halide such as stannic chloride pentahydrate, stannic bromide pentahydrate, stannic iodide pentahydrate, may also be used although not necessarily with equivalent results. As was previously set forth, it was unexpected that a transesterification of an ester by treatment of the ester with an olefin could be effected by utilizing only a catalytic amount of the tin halide rather than a stoichiometric amount based upon the olefin.

The process of this invention may be effected in any suitable manner and may comprise either a batch or continuous type operation. For example, when a batch type operation is used, a quantity of the reactants, namely, the olefin and the ester of the type hereinbefore set forth in greater detail are placed in an appropriate apparatus which may comprise a flask or, if superatmospheric pressures are to be employed, an autoclave of the rotating or mixing type. Following this, the catalytic amount of the tin halide is added at which time, due to the exothermic nature of the reaction, a rise in temperature usually occurs or, the ester may be gradually added to a stirred mixture of the olefin and the catalyst. The temperature at which the reaction is effected may be controlled by external means, that is, either cooling means if it is desired to effect the reaction at room temperature or below, or conversely, heating means if temperatures ranging from about 50° to about 100° C. are desired. The reaction is allowed to proceed for a predetermined period of time which may range from about 0.5 up to about 20 hours or more in duration, said residence time being dependent upon the various parameters of the reaction including temperature, pressure and type of reactants employed. In the event that superatmospheric pressure are employed, these pressures are afforded by introducing a substantially inert gas such as nitrogen into the reaction apparatus. Upon completion of the desired residence time, heating or cooling is discontinued and the apparatus and contents thereof are allowed to return to room temperature. The reaction mixture is then recovered and subjected to conventional means of separation such as fractional distillation whereby the desired products are recovered.

It is also contemplated within the scope of this invention that the process in which an olefin is treated with an ester may be effected in a continuous manner of operation. When such a type of operation is employed, the starting materials comprising the ester and the olefin are continuously charged to a reaction zone which is maintained at the proper operating conditions of temperature and pressure. In addition, the tin halide catalyst is also charged to the reactor through a separate line or, if so desired, it may be admixed with one or both of the reactants and the resulting mixture charged thereto in a single stream. Alternatively, the catalyst may be added to one of the reactants and the mixture charged through one line, the other reactant being charged to the reactor through another line. Upon completion of the desired residence time, the reactor effluent is continuously withdrawn and subjected to conventional means of separation whereby the desired product is separated and recovered while any unreacted starting materials may be recycled to form a portion of the feed stock.

The following examples are given for purposes of illustrating the process of the present invention in which a transesterification of an ester may be effected by reacting said ester with an olefin in the presence of certain catalytic compositions of matter. However, these examples are given merely for purposes of illustration and the present invention is not necessarily limited thereto.

EXAMPLE I

To the glass liner of a rotating autoclave was added 25 grams (0.12 mole) of 7-tetradecene, 15 grams (0.11 mole) of cyclohexyl acetate along with 5 grams (0.019 mole) of anhydrous stannic chloride. The autoclave was sealed and 30 atmospheres of nitrogen was pressed in. Following this, the autoclave was rotated and heated to a temperature of 99° C., said autoclave and contents thereof being maintained at a temperature in the range of from 99°–104° C. for a period of 4 hours. During this time, the maximum pressure in the autoclave rose to 45 atmospheres. At the end of the 4-hour period, heating was discontinued and the autoclave and contents thereof were allowed to return to room temperature, the final pressure at room temperature being 30 atmospheres. The autoclave was allowed to stand under this pressure for a period of 16 hours, at the end of which time the pressure was discharged and the autoclave was opened. The reaction mixture was recovered and analyzed by means of gas-liquid chromatography, said analysis disclosing the presence of tetradecyl acetate along with a minor portion of tetradecyl chloride.

When the above experiment was repeated utilizing 16 grams (0.08 mole) of 7-tetradecene, 39 grams (0.27 mole) of cyclohexyl acetate and 6 grams (0.023 mole) of anhydrous stannic chloride, it was found that the tetradecyl chloride formation was decreased with an increase in the formation of the desired product, namely, tetradecyl acetate.

EXAMPLE II

In this example 164 grams (1.0 mole) of isopropyl benzoate is placed in the glass liner of a rotating autoclave along with 240 grams (1.5 moles) of 1-decene and 26 grams (0.10 mole) of anhydrous stannic chloride. The autoclave is sealed and 22 grams (0.4 mole) of 2-butene is pressed in. The autoclave is then heated to a temperature of 100° C. and maintained thereat for a period of 4 hours. Following this 4-hour period, heating of the autoclave may be discontinued and the autoclave allowed to return to room temperature. After returning to room temperature and standing for a period of 16 hours, the autoclave may be opened and the reaction mixture recovered therefrom. The desired product comprising decyl benzoate may then be recovered from the mixture.

EXAMPLE III

To an Erlenmeyer flask provided with a magnetic bar for stirring the reactants may be added 49 grams (0.35 mole) of 5-decene and 75 grams (0.74 mole) of propyl acetate. Following this, 9 grams (0.03 mole) of stannic chloride may be added dropwise during a period of 5 minutes to the stirred mixture of the reactants. Due to the exothermicity of the reaction, the temperature may rise to about 45° C. and may be maintained thereat for a period of 4 hours while constantly stirring the reaction mixture. At the end of this 4-hour period, heating is discontinued and the desired product comprising decyl acetate may be recovered from the mixture.

EXAMPLE IV

To the glass liner of a rotating autoclave may be added 28 grams (0.25 mole) of 1-octene and 102 grams (0.8 mole) of butyl formate along with 9 grams of stannic chloride pentahydrate. The autoclave may then be sealed and nitrogen pressed in until an initial operating pressure of 30 atmospheres is reached. Following this the autoclave and contents may be heated to a temperature of 100° C. and maintained at this temperature for a period of 4 hours, the autoclave and contents being constantly rotated during this residence time. At the end of the aforementioned time period, heating is discontinued and the autoclave may be returned to room temperature, after which the excess pressure is discharged and the autoclave is opened. The desired product comprising octyl formate may then be recovered from the reaction mixture.

EXAMPLE V

In a manner similar to that set forth in the above examples, 16 grams (0.2 mole) of cyclohexene and 80 grams (0.8 mole) of ethyl benzoate along with 13 grams (0.03 mole) of stannic bromide are placed in the glass liner of a rotating autoclave. Following this the autoclave may be sealed and nitrogen pressed in until an initial operating pressure of 30 atmospheres is reached. The autoclave may then be heated to a temperature of 125° C. and maintained in a range of from about 125°–130° C. for a period of 4 hours. Thereafter heating is discontinued and the autoclave may be allowed to return to room temperature. The excess pressure may be discharged and the autoclave opened. The desired product comprising cyclohexyl benzoate may then be recovered from the mixture.

I claim as my invention:

1. A process for the transesterification of a carboxylic acid ester of an alkyl-, cycloalkyl- or aralkyl- alcohol containing at least two carbon atoms in the alkyl moiety with an olefin selected from the group consisting of alkenes containing two to twenty carbon atoms and cycloalkenes containing four to eight carbon atoms which comprises reacting said ester with said olefin containing a greater number of carbon atoms than said alcohol in the presence of a catalytic amount of tin halide, wherein said amount of tin halide is stoichiometrically less than the stoichiometric amount of said olefin, at a temperature in the range of from about 0° C to about 150° C and a pressure in the range of from about atmospheric to about 100 atmospheres, and recovering the resultant esterified olefin.

2. The process as set forth in claim 1 in which said tin halide is anhydrous stannic chloride.

3. The process as set forth in claim 1 in which said tin halide is stannic chloride pentahydrate.

4. The process as set forth in claim 1 in which said tin halide is stannic bromide.

5. The process as set forth in claim 1 in which said olefin is 7-tetradecene, said ester is cyclohexyl acetate and said esterified olefin is tetradecyl acetate.

6. The process as set forth in claim 1 in which said olefin is 1-decene, said ester is isopropyl benzoate and said esterified olefin is butyl benzoate.

7. The process as set forth in claim 1 in which said olefin is 5-decene, said ester is isopropyl acetate and said esterified olefin is decyl acetate.

8. The process as set forth in claim 1 in which said olefin is 1-octene, said ester is butyl formate and said esterified olefin is octyl formate.

9. The process as set forth in claim 1 in which said olefin is cyclohexene, said ester is ethyl benzoate and said esterified olefin is cyclohexyl benzoate.

* * * * *